(12) United States Patent
Grueebler et al.

(10) Patent No.: US 12,629,174 B2
(45) Date of Patent: May 19, 2026

(54) DYNAMICALLY ADJUSTABLE STIFFENING SLEEVE

(71) Applicant: Alcon Inc., Fribourg (CH)

(72) Inventors: Reto Grueebler, Greifensee (CH);
Klaus Dorawa, Kiel (DE)

(73) Assignee: Alcon Inc., Fribourg (CH)

( * ) Notice: Subject to any disclaimer, the term of this patent is extended or adjusted under 35 U.S.C. 154(b) by 896 days.

(21) Appl. No.: 17/644,200

(22) Filed: Dec. 14, 2021

(65) Prior Publication Data

US 2022/0192706 A1 Jun. 23, 2022

Related U.S. Application Data

(60) Provisional application No. 63/126,731, filed on Dec. 17, 2020.

(51) Int. Cl.
*A61B 17/34* (2006.01)
*A61B 18/00* (2006.01)
*A61F 9/007* (2006.01)

(52) U.S. Cl.
CPC ...... *A61B 17/3496* (2013.01); *A61F 9/00763* (2013.01); *A61B 2017/3443* (2013.01); *A61B 2017/3445* (2013.01)

(58) Field of Classification Search
CPC ........ A61B 17/3496; A61B 2017/3443; A61B 2017/3445; A61B 2018/00196; A61B 17/3494; A61F 9/00763; A61F 9/00736
See application file for complete search history.

(56) References Cited

U.S. PATENT DOCUMENTS

| | | |
|---|---|---|
| 3,805,787 A | 4/1974 | Banko |
| 4,030,567 A | 6/1977 | Kondo |
| 5,019,035 A | 5/1991 | Missirlian |
| 5,190,050 A | 3/1993 | Nitzsche |
| 5,217,465 A | 6/1993 | Steppe |
| 5,370,658 A | 12/1994 | Scheller |
| 5,396,880 A | 3/1995 | Kagan et al. |
| 6,312,402 B1 | 11/2001 | Hansmann |
| 6,575,989 B1 | 6/2003 | Scheller |
| 6,749,601 B2 | 6/2004 | Chin |
| 6,908,476 B2 | 6/2005 | Jud |
| 6,945,984 B2 | 9/2005 | Arumi |

(Continued)

FOREIGN PATENT DOCUMENTS

| | | |
|---|---|---|
| CN | 202426711 U | 9/2012 |
| CN | 207755450 U | 8/2018 |

(Continued)

*Primary Examiner* — Chelsea E Stinson
*Assistant Examiner* — Hamza A Darb
(74) *Attorney, Agent, or Firm* — Patterson + Sheridan, LLP

(57) ABSTRACT

A surgical tool with a stiffening sleeve that is dynamically retractable during surgery. The tool includes a needle or implement for performing minimally invasive surgery through a pre-placed cannula at a surgical site. A stiffening sleeve of the tool about the implement may provide an added degree of stiffness such as where the implement is particularly thin. However, an end of the sleeve is held in position at the cannula as the implement advances therebeyond for the surgery. Nevertheless, as determined by the surgeon, the implement may be further advanced with a corresponding and deliberate retraction of the sleeve into the tool body as desired.

15 Claims, 8 Drawing Sheets

(56) References Cited

U.S. PATENT DOCUMENTS

| | | | |
|---|---|---|---|
| 7,198,625 | B1 | 4/2007 | Hui et al. |
| 7,207,980 | B2 | 4/2007 | Christian |
| 7,338,494 | B2 | 3/2008 | Ryan |
| 7,909,816 | B2 | 3/2011 | Buzawa |
| 8,038,692 | B2 | 10/2011 | Valencia |
| 8,187,293 | B2 | 5/2012 | Kirchhevel |
| 8,202,277 | B2 | 6/2012 | Ryan |
| 8,308,737 | B2 | 11/2012 | Ryan |
| 8,845,666 | B2 | 9/2014 | Underwood |
| 8,894,636 | B2 | 11/2014 | Gille et al. |
| 9,060,841 | B2 | 6/2015 | Mccawley |
| 9,138,346 | B2 | 9/2015 | Scheller |
| 9,370,447 | B2 | 6/2016 | Mansour |
| 9,585,788 | B2 | 3/2017 | Underwood |
| 9,757,274 | B2 | 9/2017 | Scheller et al. |
| 9,775,943 | B2 | 10/2017 | Scheller |
| 9,795,505 | B2 | 10/2017 | Yu et al. |
| 9,925,326 | B2 | 3/2018 | Scheller |
| 9,931,244 | B2 | 4/2018 | Ryan |
| 9,949,876 | B2 | 4/2018 | Mansour |
| 10,045,883 | B2 | 8/2018 | Egli |
| 10,085,883 | B2 | 10/2018 | Auld |
| 10,179,007 | B2 | 1/2019 | Peterson |
| 10,285,583 | B2 | 5/2019 | Parto |
| 10,376,315 | B2 | 8/2019 | Scheller et al. |
| 10,391,232 | B2 | 8/2019 | Scheller et al. |
| 10,413,445 | B2 | 9/2019 | Scheller et al. |
| 10,413,446 | B2 | 9/2019 | Bouch et al. |
| 10,617,560 | B2 | 4/2020 | Ryan |
| 10,639,197 | B2 | 5/2020 | Lopez |
| 10,675,181 | B2 | 6/2020 | Murakami |
| 10,828,192 | B2 | 11/2020 | Scheller et al. |
| 10,898,373 | B2 | 1/2021 | Ryan |
| 10,945,882 | B2 | 3/2021 | Ryan |
| 11,020,270 | B1 | 6/2021 | Peyman |
| 11,278,449 | B2 | 3/2022 | Ryan |
| 2003/0195539 | A1 | 10/2003 | Attinger |
| 2005/0033309 | A1 | 2/2005 | Ryan |
| 2005/0209618 | A1 | 9/2005 | Auld |
| 2007/0099149 | A1 | 5/2007 | Levy et al. |
| 2007/0106300 | A1 | 5/2007 | Auld |
| 2007/0255196 | A1 | 11/2007 | Wuchinich |
| 2008/0195135 | A1 | 8/2008 | Attinger |
| 2008/0255526 | A1 | 10/2008 | Bosse et al. |
| 2009/0093800 | A1 | 4/2009 | Auld |
| 2009/0131870 | A1 | 5/2009 | Fiser |
| 2010/0063359 | A1 | 3/2010 | Okoniewski |
| 2010/0228226 | A1 | 9/2010 | Nielsen |
| 2011/0196410 | A1* | 8/2011 | Besselink ............ A61M 29/02 |
| | | | 606/191 |
| 2012/0116361 | A1 | 5/2012 | Hanlon et al. |

| | | | |
|---|---|---|---|
| 2012/0209167 | A1* | 8/2012 | Weber ................ A61B 17/3474 |
| | | | 604/170.01 |
| 2013/0090531 | A1 | 4/2013 | Ryan |
| 2013/0090635 | A1 | 4/2013 | Mansour |
| 2013/0197488 | A1 | 8/2013 | Scheller et al. |
| 2013/0281817 | A1 | 10/2013 | Schaller |
| 2014/0121469 | A1 | 5/2014 | Alcon |
| 2014/0128896 | A1 | 5/2014 | Ryan |
| 2015/0231687 | A1 | 8/2015 | Ookubo et al. |
| 2016/0022256 | A1* | 1/2016 | Peterson ................. A61F 9/007 |
| | | | 600/204 |
| 2017/0215855 | A1 | 8/2017 | Nunan |
| 2017/0333251 | A1 | 11/2017 | Scheller et al. |
| 2018/0214307 | A1 | 8/2018 | Ryan |
| 2018/0228651 | A1 | 8/2018 | Mansour |
| 2018/0250164 | A1 | 9/2018 | Ryan |
| 2018/0360660 | A1 | 12/2018 | Lopez |
| 2019/0059936 | A1 | 2/2019 | Ryan |
| 2019/0269556 | A1 | 9/2019 | Meckel |
| 2019/0282322 | A1 | 9/2019 | Mirsepassi |
| 2019/0374249 | A1 | 12/2019 | Abt et al. |
| 2020/0163717 | A1 | 5/2020 | Hartkopf-Ceylan |
| 2020/0197217 | A1 | 6/2020 | Ryan |
| 2021/0177652 | A1 | 6/2021 | Chen et al. |
| 2021/0177653 | A1 | 6/2021 | Hallen |
| 2021/0244567 | A1 | 8/2021 | Ryan |
| 2021/0251805 | A1 | 8/2021 | Ryan |
| 2021/0290438 | A1 | 9/2021 | Hallen |
| 2022/0031509 | A1 | 2/2022 | Tazawa |
| 2022/0192706 | A1 | 6/2022 | Grueebler et al. |

FOREIGN PATENT DOCUMENTS

| | | | |
|---|---|---|---|
| DE | 651436 | C | 10/1937 |
| EP | 1782781 | A1 | 5/2007 |
| EP | 1955684 | A1 | 8/2008 |
| EP | 2760400 | B1 | 1/2018 |
| EP | 3319564 | B1 | 11/2019 |
| EP | 3191161 | B1 | 1/2020 |
| EP | 3656332 | A1 | 5/2020 |
| EP | 3352682 | B1 | 7/2020 |
| EP | 3332756 | B1 | 8/2020 |
| GB | 1448129 | A | 9/1976 |
| JP | 2009072221 | A | 4/2009 |
| JP | 2020044289 | A | 3/2020 |
| JP | 2022040303 | A | 3/2022 |
| WO | 0119255 | A1 | 3/2001 |
| WO | 2010064670 | A1 | 6/2010 |
| WO | 2013133712 | A1 | 9/2013 |
| WO | 2016019160 | A1 | 2/2016 |
| WO | 2017053832 | A1 | 3/2017 |
| WO | 2017075514 | A1 | 5/2017 |

* cited by examiner

DYNAMICALLY ADJUSTABLE STIFFENING SLEEVE

PRIORITY CLAIM

This application claims the benefit of priority of U.S. Provisional Patent Application Ser. No. 63/126,731 titled "DYNAMICALLY ADJUSTABLE STIFFENING SLEEVE," filed on Dec. 17, 2020, whose inventors are Reto Grüebler and Klaus Dorawa, which is hereby incorporated by reference in its entirety as though fully and completely set forth herein.

BACKGROUND

Over the years, many dramatic advancements in the field of minimally invasive surgical procedures have taken place. Accordingly, natural patient injury and healing times have been dramatically reduced. In the area of eye surgery as an example, previously inaccessible injured or deteriorating tissue may be repaired or directly serviced through minimally invasive procedures. When the eye surgery includes accessing the retina, it is common that a vitrectomy will be included in at least part of the procedure. Vitrectomy is the removal of some or all of the vitreous humor from a patient's eye. In some cases, where the surgery was limited to removal of clouded vitreous humor, the vitrectomy may constitute the majority of the procedure. However, a vitrectomy may accompany surgery to repair a retina, to address a macular pucker, or a host of other issues.

In keeping with the example of eye surgery and a vitrectomy, the vitreous humor itself is a clear gel that may be removed by an elongated needle when inserted through a pre-placed cannula at the eye. More specifically, a vitrectomy probe is a surgical tool that is held by a surgeon at a gripping location with a needle emerging from the tool as described. The needle includes a central channel for removal of the vitreous humor. Further, the cannula provides a structurally supportive conduit strategically located at an offset location at the front of the eye, such as the pars plana. In this way, the probe needle may be guidingly inserted into the eye in a manner that avoids damage to the patient's lens or cornea.

The needle is generally guided and supported by a cannula and trocar assembly which has been prepositioned at the location of an incision through the pars plana as indicated. Thus, the needle may be securely advanced through to the interior of the eye to perform the surgical procedure. Of course, just as with a probe needle for a vitrectomy, a variety of other surgical implements may be similarly advanced through a cannula and trocar assembly for a variety of different surgical purposes. These may include forceps, scissors, light instruments and other instrumentation.

Over the years, minimally invasive surgeries, such as the described vitrectomies, have employed smaller and smaller implements for increasingly precise surgical maneuvers. For example, vitrectomy probe needles that traditionally may have been about 23 gauge may be about 25 or 27 gauge. This translates to reducing a needle diameter from just under about 0.5 mm to less than about 0.4 mm. Considering that a vitrectomy probe needle is likely to be hollow, this increasingly thin gauge implement may be pliable. For other instruments, a similar pliability issue may emerge as the implement size becomes increasingly smaller, including for a vitrectomy probe needle.

Increased pliability or flexibility for a surgical implement is not necessarily helpful to a surgeon during a procedure.

Generally speaking, the surgeon may be better aided by a degree of rigidity in the implement that affords a greater degree of control. That is, manual manipulation of the implement by the surgeon at an exterior location is more likely to reliably transfer to the surgical site if the implement is more inflexible. So, for example, in the case of a vitrectomy procedure, the probe may include a grip from which the needle extends toward and through the noted cannula structure at the eye. A larger and more rigid stiffening sleeve may extend from the structural support of the cannula and back toward the body and grip of the tool. Thus, at least in the space between the surgeon's grip location and the front of the eye, bending of the needle may be avoided due to the presence of the stiffening sleeve. Rather, a secure and reliably linear translation of movement from the grip to a pivot location at the surface of the eye is displayed (e.g. where the stiffening sleeve contacts the cannula). Once more, the actual length of the needle which presents within the eye and is not structurally bound by the stiffening sleeve is limited. Thus, bending of the needle is further minimized. Unfortunately, utilizing a stiffening sleeve as detailed, may reduce the available workable length of the needle in the eye because the sleeve outer diameter may not fit through the cannula.

SUMMARY

A surgical tool is provided. The tool includes a gripping element that is manually secured by a surgeon such that a surgical implement may extend from the element for the sake of surgical access to a tissue region of a patient. A stiffening sleeve is provided about the implement for stabilization thereof during a surgical procedure at the region with the implement. A biasing mechanism is coupled to the sleeve which extends the sleeve a maximum from the element but allows for retractability into the element in response to the implement contacting a structure at the tissue region.

DETAILED DESCRIPTION

In the following description, numerous details are set forth to provide an understanding of the present disclosure.

However, it will be understood by those skilled in the art that the embodiments described may be practiced without these particular details. Further, numerous variations or modifications may be employed which remain contemplated by the embodiments as specifically described.

Embodiments are described with reference to certain types of surgical procedures. In particular, a forceps tool is illustrated at FIGS. 2a-d whereas a vitrectomy tool in which vitreous humor is removed to address vitreous hemorrhage is illustrated at FIGS. 1, 3 and 4A and 4B. However, tools and techniques detailed herein may be employed in a variety of other manners as well. For example, the implement reaching into the eye for the procedure may be a forceps, a vitrectomy probe, scissors, etc. Further, while a vitrectomy procedure is largely discussed herein, embodiments of a vitrectomy probe as detailed herein may be utilized to address retinal detachments, macular pucker, macular holes, vitreous floaters, diabetic retinopathy or a variety of other eye conditions. Additionally, while vitrectomy and other eye surgeries often benefit from the use of fairly thin implements, other types of surgeries may benefit from the unique architecture and techniques detailed herein. Indeed, so long as a supportive stiffening sleeve is employed that is dynamically adjustable during surgery, appreciable benefit may be realized.

Figure 1:
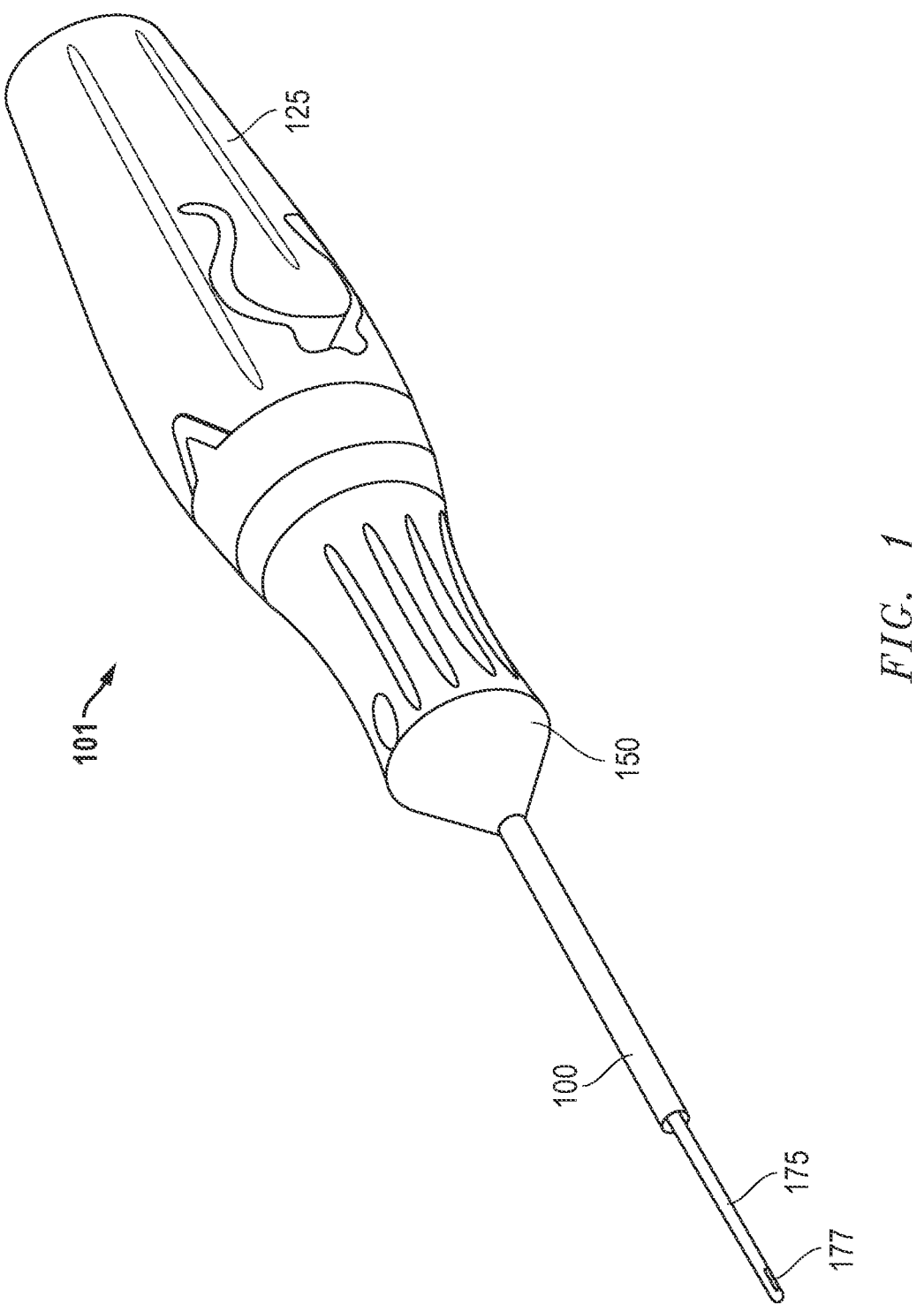
FIG. 1 is a side perspective view of a surgical tool employing a needle aided by an embodiment of a dynamically adjustable stiffening sleeve.

Referring now to FIG. 1, a side perspective view of a surgical tool 101 is illustrated which employs a needle 175 aided by an embodiment of a dynamically adjustable stiffening sleeve 100. In the embodiment shown, the tool 101 is a vitrectomy probe that may be utilized in a procedure as detailed further herein. However, other types of instruments for a variety of different surgical applications may take advantage of such a dynamically adjustable stiffening sleeve 100. For example, as with many other surgical tools, the probe 101 is outfitted with an implement (e.g. the needle 175) that is particularly thin (e.g., 20 gauge or smaller sizing). Thus, even where stainless steel or other suitably durable surgical materials are employed, the needle 175 alone may lack a desired rigidity from the surgeon's perspective and be prone to a degree of bending.

The noted lack of rigidity displayed by the needle 175 may be addressed by the inclusion of the illustrated sleeve 100 about the needle 175. However, unlike a conventional sleeve, the illustrated sleeve 100 is dynamically adjustable in terms of the length or distance it may extend from the probe 101 at its gripping element 150. Thus, as detailed below, the surgeon may advantageously exert control over how much sleeve support is provided versus how much reach may be attained by the needle 175. This may take place in a dynamic fashion with the reach of the needle 175 changing throughout the course of a given surgical procedure. It is worth noting that the dynamically adjustable length of the sleeve 100 is referenced herein with respect to its extension from a gripping element 150 of the tool 101. This is meant to infer and include any distal-most body portion of the tool 101 from which the sleeve 100 might extend, whether or not such feature is generally thought of as "gripping" in nature.

Continuing with reference to FIG. 1, the tool 101 includes a shell 125, rearward of the gripping element 150. So, for example, in the case of a vitrectomy probe, the surgeon may hold the instrument at the gripping element 150, between a thumb and index finger with the shell resting at the perlicue of the hand and protectively encasing instrument components therein. The needle 175 may support a cutter therein which interacts with a port 177 thereof for the controlled uptake of vitreous humor as described further below. For such a procedure, it is the dynamically positionable nature of the stiffening sleeve 100 that uniquely supports and facilitates the surgeon's efforts in this endeavor.

Figure 2A:
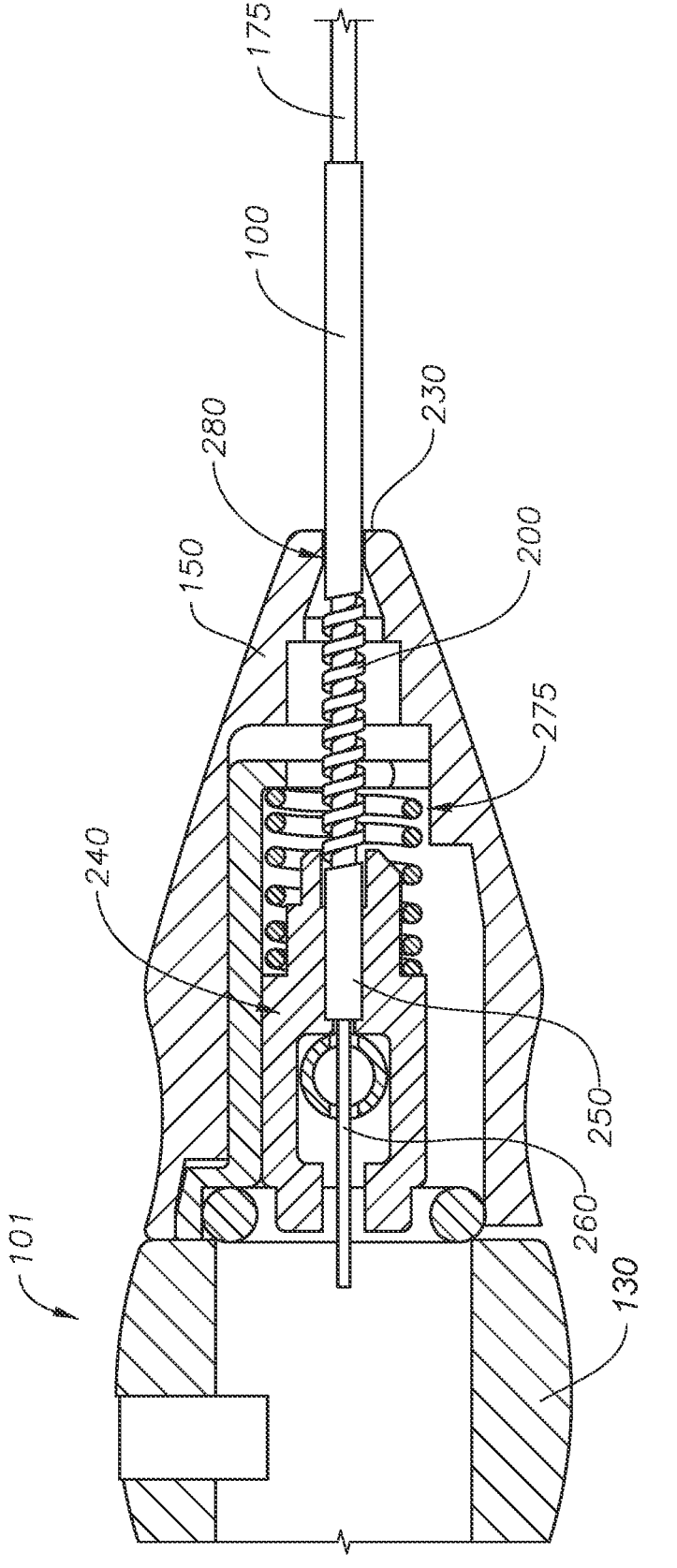
FIG. 2a is a side cross-sectional view of a first embodiment of the stiffening sleeve in an extended configuration.
Figure 2B:
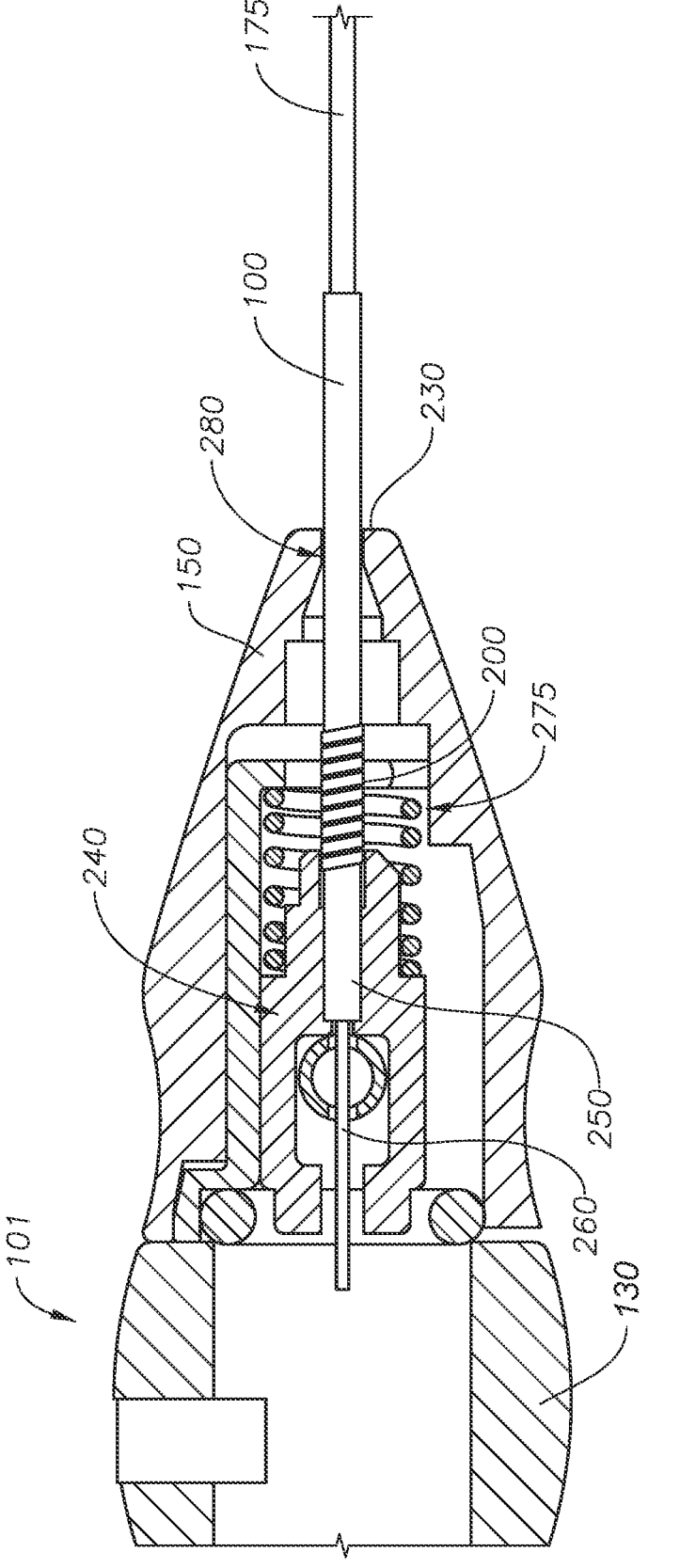
FIG. 2b is a side cross-sectional view of the first embodiment of the stiffening sleeve in a compressed configuration.

Referring now to FIG. 2a, a side cross-sectional view of another tool 101 (forceps) is shown. In this depiction, the internal architecture of a first embodiment of the stiffening sleeve 100 is visible. Namely, a biasing mechanism 200 is shown that facilitates dynamic travel of the stiffening sleeve 100 during a surgical procedure. So, for example, in one embodiment, the stiffening sleeve 100 may extend anywhere from 4-6 mm when at rest (other shorter and longer lengths are also contemplated). For example, the stiffening sleeve may extend 2 mm, 0.5 cm (centimeter), 1 cm, 1.5 cm, 2 cm, 2.5 cm, 3 cm, 3.5 cm, etc.). Nevertheless, as a given surgical procedure dictates, the sleeve 100 may retract into the probe 101 (e.g., as seen in FIG. 2b) by several centimeters (cm) or millimeters, perhaps only extending from the end 230 of the gripping element 150 by about one mm or less when fully retracted. As discussed further below, such a retraction or degree of "travel" by the sleeve 100 would translate into a corresponding extension or exposure of the needle 175 to facilitate surgical access during the surgical procedure. Of course, where a larger degree of travel is desired, the biasing mechanism 200 may include a longer spring or perhaps even a plurality of aligned springs.

Figure 2C:
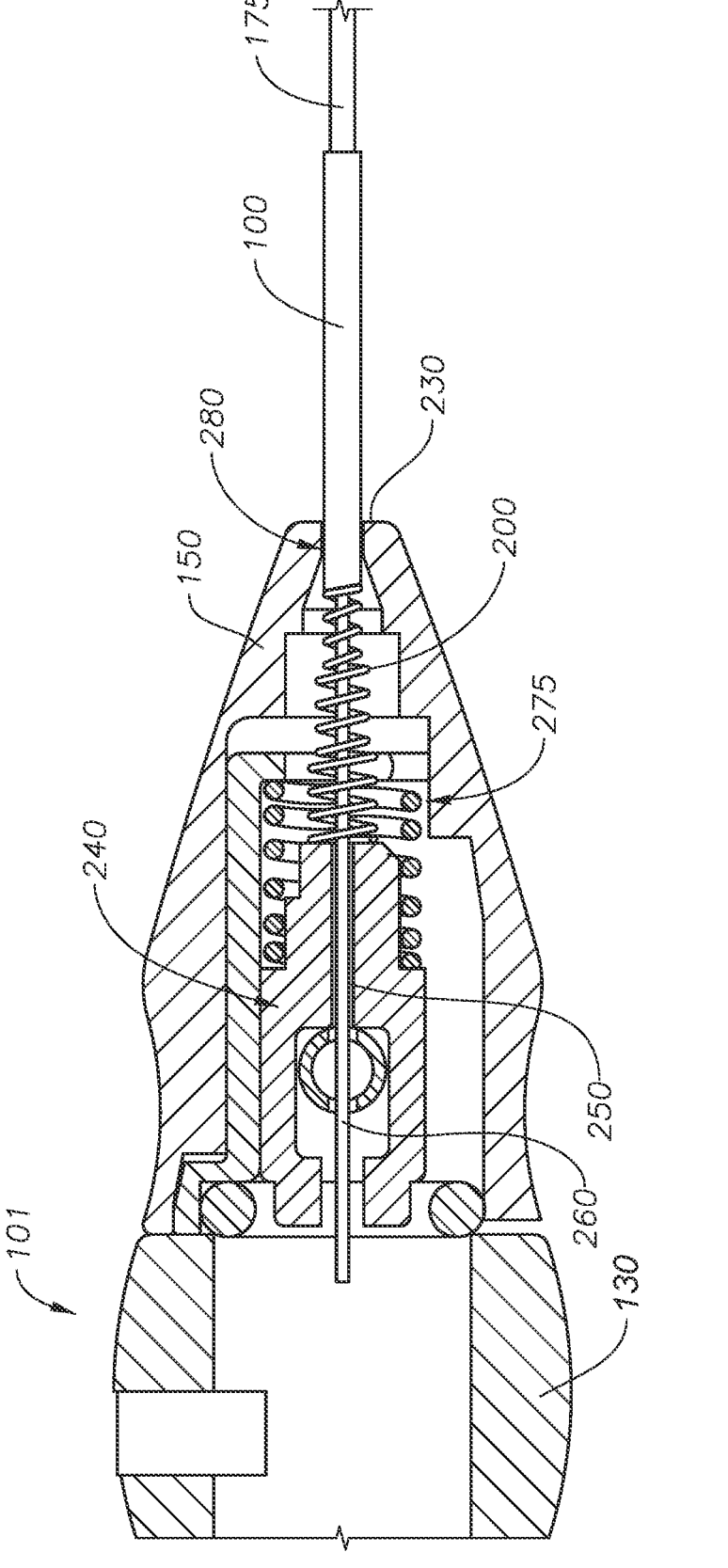
FIG. 2c is a side cross-sectional view of a second embodiment of the stiffening sleeve in an extended configuration.
Figure 2D:
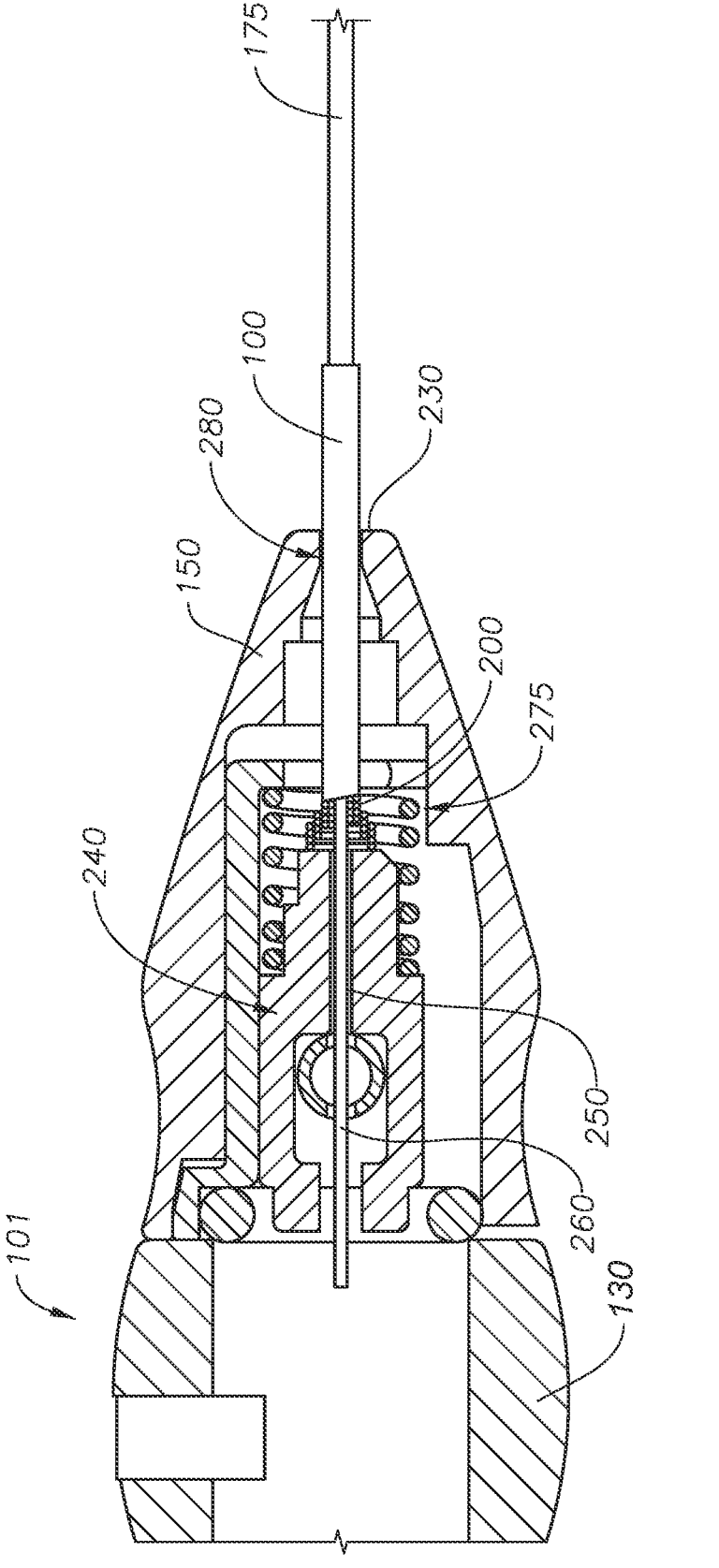
FIG. 2d is a side cross-sectional view of the second embodiment of the stiffening sleeve in a compressed configuration.

As seen in FIGS. 2c-d, a spring with different diameters may be used as the biasing mechanism. FIG. 2c illustrates the biasing mechanism (in this case, a spring) in an extended position showing a series of three diameter sections (from small to large progressing from the stiffener to the base). Other numbers of diameters (e.g., 2, 4, 5, 10, etc.) can also be used. By using different diameters, the spring may collapse further in on itself when the spring is compressed. For example, as seen in FIG. 2d, the springs are shown in cross section to show that the smaller diameter spring section has compressed partially into the intermediate diameter spring section which has compressed partially into the larger diameter spring section. This may result in a final compressed spring length that is smaller than if the spring had been one continuous diameter (as seen in FIGS. 2a-b).

Continuing with reference to FIGS. 2a-d, the biasing mechanism 200 illustrated is a spring that is in monolithic axial alignment with the stiffening sleeve 100 so as to provide the positional dynamic character thereto. Support is drawn from a base 250 mounted within a component housing 240 of the probe 101. As illustrated, the base 250 is also in monolithic axial alignment with the spring 200 and sleeve 100 such that all three features may be provided as a single unitary component for assembly with the probe 101. In some embodiments, the unitary sleeve and spring may be made of stainless steel, cobalt steel, or nitinol. Other materials are also contemplated (e.g., other metals or plastic such as high-density polyethylene (HDPE), polyvinyl chloride (PVC), or polycarbonate (PC)). In some embodiments, the length of the spring 200 may be short enough to insure that the spring 200 does not extend past the end 230 even when fully extended. In some embodiments, the space between coils in the spring 200 may be selected based on the degree of retraction or extension required of the spring 200. In some embodiments, an interface 280 between the sleeve 100 and the end 230 may include a slight friction fit such that the sleeve 100 can move relative to the interface 280 without a large degree of side-to-side (perpendicular to the outer sleeve surface) movement. In some embodiments, the interface 280 may include additional space between the sleeve 100 and the base 230 to allow faster spring response (at the expense of some slight additional side-to-side movement).

In some embodiments, a lubricant may be added to the interface 280 (or the surface of the sleeve 100 at the interface 280 may be smoothed to reduce friction between the sleeve 100 and the end 230.

FIGS. 2a-d also reveal other internal features such as a probe spring 275 that further biases the secured base 250 for dampening spring movements. A cutter 260, ultimately for reciprocation within the needle 175 in support of a vitrectomy procedure is also apparent. In this regard, the cutter 260 may be reciprocated by other mechanical components internal to the probe. A cross-section of the proximal end 130 and manner of coupling to the gripping element 150 is also apparent with reference to FIGS. 2a-d. In some embodiments, proximal end 130 may be gripped by the surgeon or may be further coupled to a handle that is gripped by the surgeon.

Figure 3:
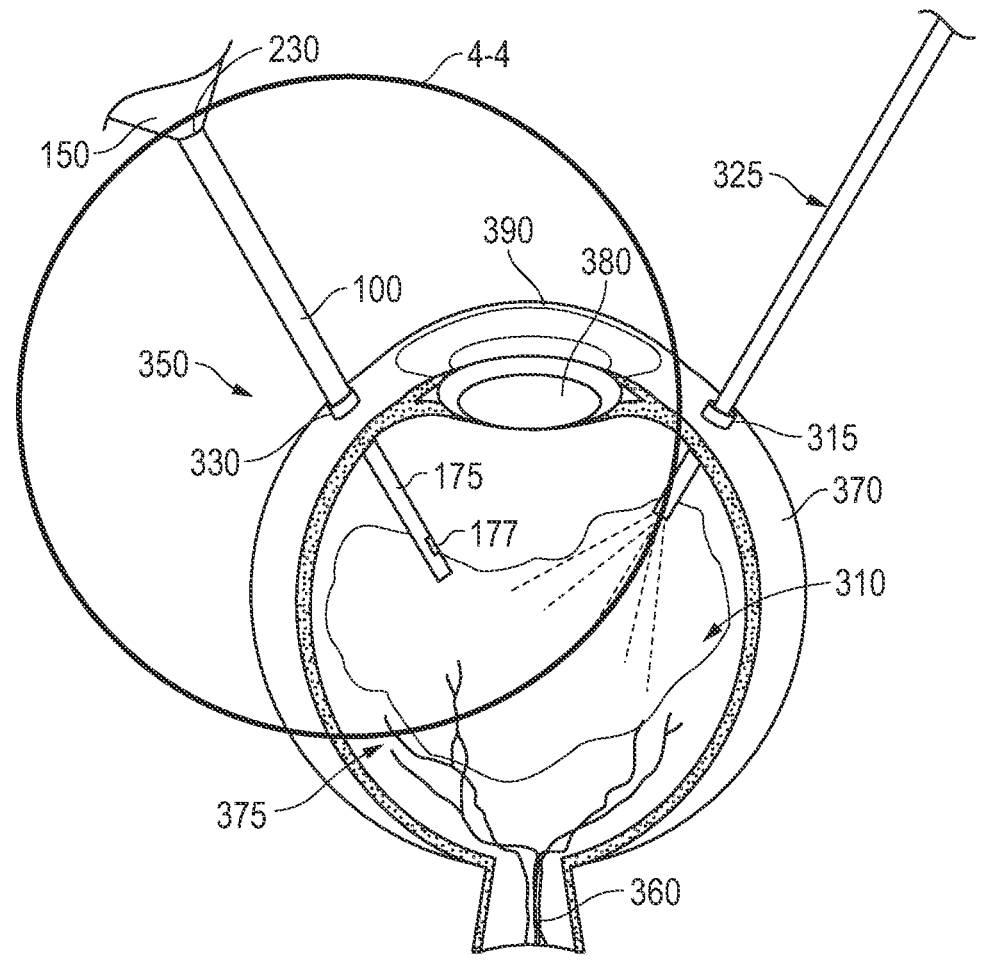
FIG. 3 is an overview illustration of a surgical procedure performed with the tool of FIG. 1 as aided by the stiffening sleeve.

Referring now to FIG. 3, an overview illustration of a surgical procedure performed with the tool 101 of FIG. 1 is shown. Notably, the procedure is aided by the stiffening sleeve 100. In this view, a side cross-sectional overview of a patient's eye 350 is shown wherein the procedure is a vitrectomy procedure. During the procedure, the needle 175 of the probe 101 is inserted through a preplaced cannula 330 and directed toward a region 310 where vitreous humor is to be removed. Specifically, as described above, a suction is applied and the port 177 is used for the uptake of the vitreous humor or other substances. For example, in the procedure illustrated, a hemorrhage may be taking place in the region 310 such that blood is drawn into the port 177 along with the vitreous humor.

Notice that while the needle 175 reaches into the interior of the eye 350 for the procedure as described, the stiffening sleeve 100 which surrounds the needle 175 does not. Rather, the end of the sleeve 100 is securely rested at the internal structure of the cannula 330. More specifically, the interior cannula structure may be of a funnel shaped or other accommodating morphology so as to receive and support the end of the stiffening sleeve 100 during the procedure. By the same token, the center of the cannula 330 includes an orifice of sufficient size to allow passage of the needle 175 therethrough. Of course, the orifice would also be too small to allow the same passage of the sleeve 100. So, for example, in one embodiment, the orifice may be about 0.475 mm in diameter so as to allow for passage of a 25 gauge and smaller needle 175 (e.g. 0.455 mm diameter or smaller). At the same time, this orifice would also prevent passage of a 23 gauge and larger sleeve 100 (e.g. 0.58 mm diameter or larger). Of course, a variety of different dimensional combinations may be employed so as to promote needle passage and prohibit sleeve passage through an orifice of the cannula 330 as described.

With the sleeve 100 stably interfacing the interior structure of the cannula 330, the surgeon may steer the needle about a pivot point at the cannula 330. In this manner, a certain stabilized working area is attained with the needle 175 at the interior of the eye 350. Further, between the cannula 330 and the tool 101 of FIG. 1, where unintended bending might otherwise be of concern, supplemental stiffness is provided by the sleeve 100.

Continuing with reference to FIG. 3, as alluded to above, a cutter is reciprocating within the needle 175 during this delicate procedure. The surgery illustrated also includes a light instrument 325 reaching into the eye 350 through another cannula 315. In both circumstances, the cannulas 315, 330 are positioned in an offset manner at the sclera 370. In this way, the more delicate cornea 390 and lens 380 may be avoided.

By the same token, the optic nerve 360 and retina 375 are also quite delicate. With this in mind, the stiffening sleeve 100 may play an initial role in preventing the needle 175 from unintentionally reaching too far into the eye 350. By the same token, however, the surgeon may exert an intentional force such that the sleeve 100 overcomes the biasing mechanism 200 at the interior of the tool 101 (see FIG. 1). Thus, as detailed further below, the sleeve 100 may dynamically retract into the gripping element 150 at the end 230 thereof to allow further intended needle 175 advancement.

Figures 4A, 4B:
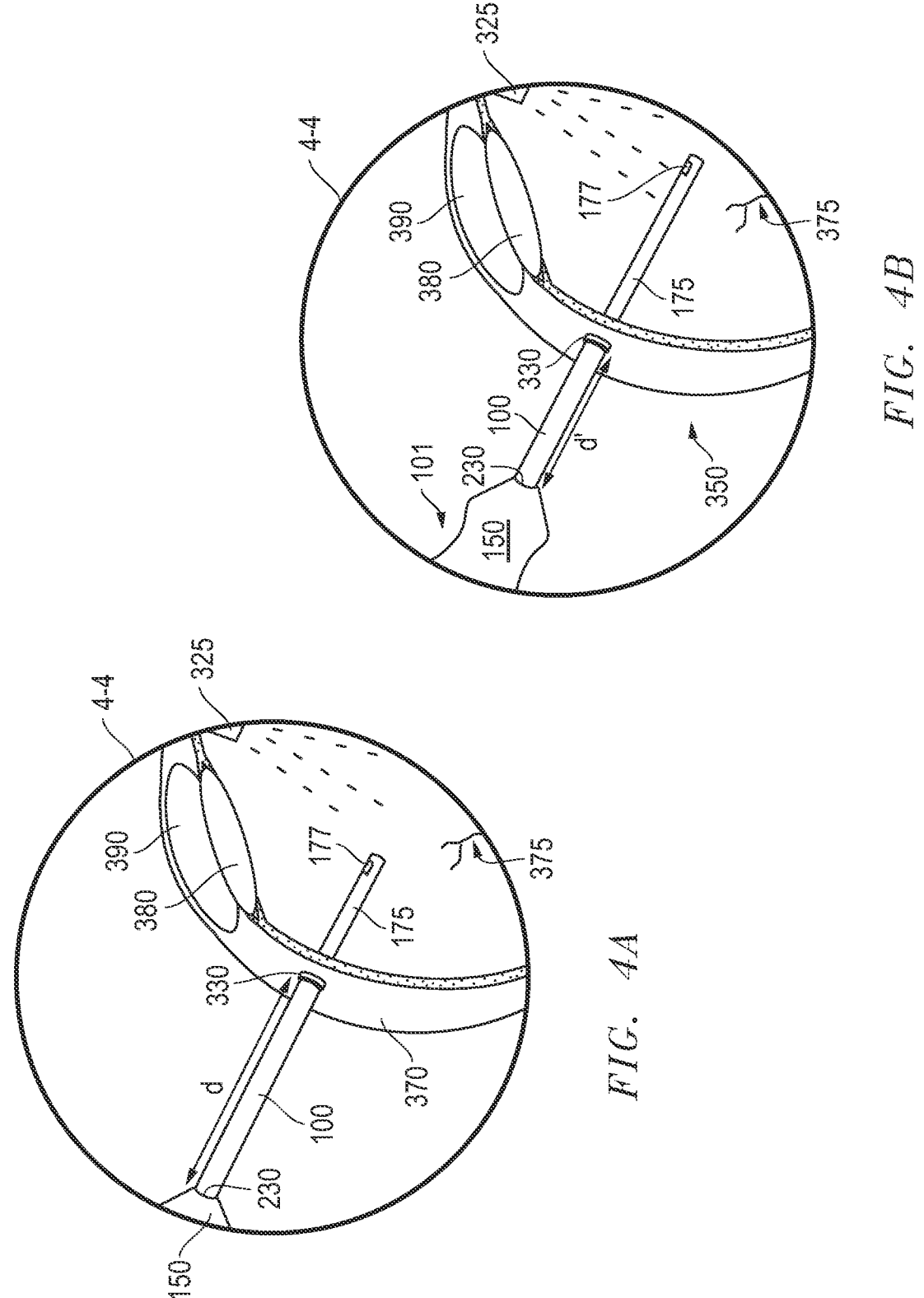
FIG. 4A is an enlarged view of the procedure of FIG. 3, taken from 4-4 thereof and illustrating the procedure with the sleeve in a first extended position.
FIG. 4B is an enlarged view of the procedure of FIG. 4A, illustrating the sleeve in a second retracted position.

Referring now to FIG. 4A, an enlarged view of the procedure of FIG. 3, taken from 4-4 thereof is shown. Specifically, FIG. 4A illustrates the procedure with the sleeve 100 in a first extended position. In the extended position, the sleeve 100 covers an extended distance (d) between the cannula 330 and the end 230 of the gripping element 150 that is substantially greater than a retracted distance (d') as shown in FIG. 4B. More specifically, FIG. 4B depicts an enlarged view of the procedure of FIG. 4A, with the sleeve 100 in a second retracted position that is intentionally directed by the surgeon during the procedure. With added reference to FIG. 2, the retracted position of the sleeve 100 retreating into the tool 101 corresponds with the internal spring 200 compressing and the needle 175 deliberately being extended further into the eye 350 by the surgeon. In one embodiment, the sleeve 100 may extend to about 5 mm or more (e.g., 1 cm, 1.5 cm, 2 cm, 2.5 cm, 3 cm, 3.5 cm, etc.) in extended distance (d) and be retracted down to no more than about 1 mm in retracted distance (d'). Of course, a variety of different ranges, maximums and minimums, may be employed in this regard.

Continuing with added reference to FIG. 2, the described procedure merely requires that the surgeon deliberately exert enough force to overcome the internal biasing mechanism 200 and extend the needle 175. In this manner, the spring 200 is sufficiently charged to substantially avoid accidental slippage but not so much as to require undue application of force by the surgeon. In this manner, the stiffening sleeve 100 may be considered reliably dynamically adjustable for the procedure as detailed herein.

Figure 5:
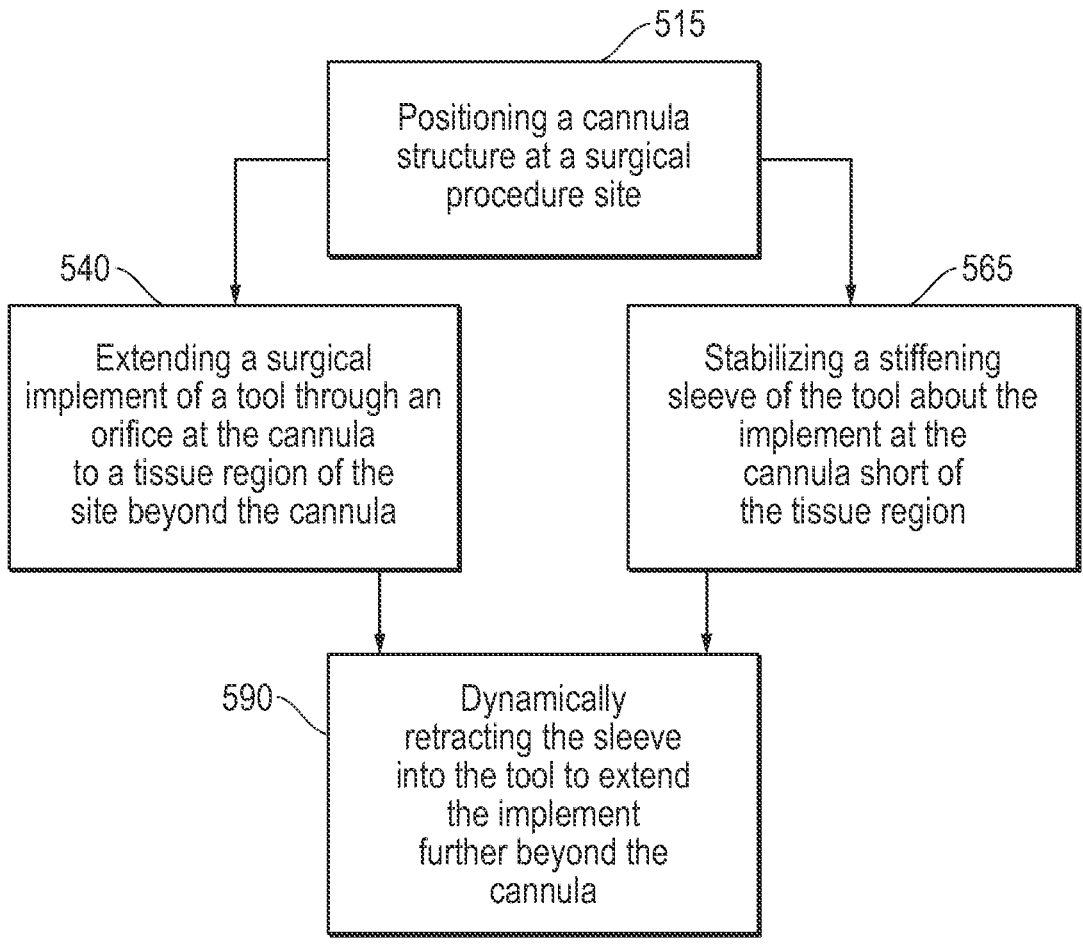
FIG. 5 is a flow-chart summarizing an embodiment of performing a minimally invasive surgical procedure with a needle aided by a dynamically adjustable stiffening sleeve.

Referring now to FIG. 5, a flow-chart summarizing an embodiment of performing a minimally invasive surgical procedure with a needle aided by a dynamically adjustable stiffening sleeve is shown. With a cannula positioned at a surgical site for supportive structure as indicated at 515, an implement such as a needle may be guided through an orifice of the cannula as noted at 540. Thus, the needle may extend from the surgical tool and beyond the cannula to a more specific tissue region. By the same token, a stiffening sleeve of the tool that is located about the needle may be stabilized by the structure of the cannula, short of the tissue region (see 565). However, without any notable sacrifice to stabilization by the sleeve on the needle, the sleeve may also be dynamically retracted into the tool by the surgeon. That is, as indicated at 590, should the surgeon desire to extend the needle further toward the tissue region, this may be achieved by the dynamic retraction of the sleeve into the tool for sake of enhanced, more precise surgical maneuvering.

Embodiments described hereinabove include architecture and techniques that allow for practical use of a stiffening sleeve to support a surgical procedure employing a relatively thin surgical implement. That is, rather than remain reliant on the length of the stiffening sleeve to determine surgical access with the implement, the sleeve is dynamically adjustable across a predetermined range. Thus, surgical access to a region of tissue may be supported across a variety of different distances as illustrated and detailed herein. This allows for flexibility in surgical tool design, for example, in terms of needle implement length. Perhaps even more notably, tool or implement changeouts may be avoided during surgery where multiple lengths or depths are at issue or where the targeted depth has been estimated with some degree of inaccuracy.

The preceding description has been presented with reference to presently preferred embodiments. However, other embodiments and/or features of the embodiments disclosed but not detailed hereinabove may be employed. Furthermore, persons skilled in the art and technology to which these embodiments pertain will appreciate that still other alterations and changes in the described structures and methods of operation may be practiced without meaningfully departing from the principle and scope of these embodiments. Additionally, the foregoing description should not be read as pertaining only to the precise structures described and shown in the accompanying drawings, but rather should be read as consistent with and as support for the following claims, which are to have their fullest and fairest scope.

The invention claimed is:

1. A surgical tool, comprising:
a tool body comprising a proximal end configured for grasping by a user and a distal end;
a surgical implement extending from the distal end of the tool body and configured to access a tissue region of a patient;
a stiffening sleeve extending from the distal end of the tool body and surrounding at least a portion of the surgical implement extending from the distal end of the tool body for stabilizing the surgical implement during a surgical procedure;
a biasing mechanism coupled to the stiffening sleeve;
a base coupled to the biasing mechanism and configured to support the biasing mechanism within the tool body; and
a dampening feature configured to bias the base to dampen movements of the biasing mechanism, wherein:
the biasing mechanism and the dampening feature extend distally from the base;
the biasing mechanism is unitary with the stiffening sleeve, and
the biasing mechanism is configured to:
allow the stiffening sleeve to retract into the distal end of the tool body in response to a force pushing the stiffening sleeve into the tool body, and
allow the stiffening sleeve to extend from the distal end of the tool body as the force is removed.

2. The surgical tool of claim 1, wherein the surgical implement is one of a vitrectomy probe, forceps, and scissors.

3. The surgical tool of claim 2, wherein the stiffening sleeve includes a travel range between a maximum extension from the tool body and fully retracting into the distal end of the tool body that is greater than about 4 mm.

4. The surgical tool of claim 2, wherein the tissue region is an eye of the patient and the surgical procedure is one of a vitrectomy and membrane removal.

5. The surgical tool of claim 1, wherein the biasing mechanism comprises at least one spring.

6. The surgical tool of claim 5, wherein the biasing mechanism is secured within the tool body of the surgical tool.

7. The surgical tool of claim 6, wherein the biasing mechanism is configured to remain inside the tool body even when fully extended.

8. The surgical tool of claim 1, wherein the biasing mechanism comprises a spring having at least two different diameter sections configured such that at least one section of the at least two different diameter sections with a smaller diameter than an adjoining section of the at least two different diameter sections with a larger diameter at least partially collapses into the adjoining section when the spring is compressed.

9. A surgical system for employing in an eye surgery, the surgical system comprising:
a cannula for inserting into an eye of a patient to provide access to an eye interior; and
a probe comprising:
an implement for extending into the eye through the cannula to perform the eye surgery;
a dynamically adjustable stiffening sleeve about the implement for contacting an inner surface of the cannula to prohibit sleeve passage therethrough with the implement;
a biasing mechanism coupled to the stiffening sleeve and configured to:
allow the stiffening sleeve to retract into a body of the probe as the implement is inserted into the eye through the cannula, and
allow the stiffening sleeve to extend from the body of the probe as the implement is removed from the cannula;
a base secured within the implement to provide support to the stiffening sleeve and the biasing mechanism; and
a dampening feature configured to bias the base to dampen movements of the biasing mechanism, wherein:
the stiffening sleeve, the base, and the biasing mechanism are in axial alignment and form a unitary monolithic component,
the biasing mechanism extends from a proximal end of the stiffening sleeve, and
the biasing mechanism and the dampening feature extend distally from the base.

10. The surgical system of claim 9, wherein:
the inner surface of the cannula comprises a funnel surface with an orifice for guiding of the implement therethrough; and
interfacing of the stiffening sleeve with the funnel surface of the cannula provides a pivot point to a surgeon for the eye surgery.

11. The surgical system of claim 10, wherein the orifice is sized to accommodate a needle smaller in diameter than about 23 gauge therethrough.

12. A method of performing surgery, comprising:
positioning a cannula by inserting the cannula into a surgical site;
extending an implement of a surgical tool through an orifice of the cannula to a tissue region of the surgical site;
stabilizing a stiffening sleeve of the surgical tool about the implement at the cannula short of the tissue region;
dynamically retracting the stiffening sleeve into a body of the surgical tool as the cannula pushes back on the stiffening sleeve against a biasing mechanism when the implement is extended into the tissue region;

dynamically extending the stiffening sleeve from the body of the surgical tool as the implement is removed from the cannula; and dampening, via a dampening feature disposed about the biasing mechanism, movements of the biasing mechanism during the dynamic retraction and dynamic extension of the stiffening sleeve;

wherein:

the stiffening sleeve and the biasing mechanism form a unitary monolithic component, and the biasing mechanism extends from a proximal end of the stiffening sleeve.

13. The method of claim 12, wherein the stabilizing comprises employing the biasing mechanism to extend the stiffening sleeve about the surgical tool.

14. The method of claim 13, wherein the dynamically retracting the stiffening sleeve comprises a surgeon pushing the stiffening sleeve against the cannula as the implement is inserted.

15. The method of claim 14, wherein the retracting of the stiffening sleeve facilitates further extending of the implement through the orifice toward the tissue region for the surgery.

* * * * *